United States Patent [19]

Ueda et al.

[11] Patent Number: 4,673,676

[45] Date of Patent: Jun. 16, 1987

[54] PYRIMIDOISOQUINOLINE DERIVATIVES USEFUL FOR TREATING ALLERGIES

[75] Inventors: Ikuo Ueda, Uenohigashi; Youichi Shiokawa, Hozumidai; Takashi Manabe, Kawanishi, all of Japan

[73] Assignee: Fujisawa Pharmaceutical Co., Ltd., Osaka, Japan

[21] Appl. No.: 669,865

[22] Filed: Nov. 9, 1984

[30] Foreign Application Priority Data

Nov. 23, 1983 [GB] United Kingdom ............... 8331228
Mar. 6, 1984 [GB] United Kingdom ............... 8405776
Oct. 12, 1984 [GB] United Kingdom ............... 8425791

[51] Int. Cl.$^4$ .................. A61K 31/505; C07D 487/04
[52] U.S. Cl. .................................. 514/267; 544/252; 546/143; 546/150
[58] Field of Search ................... 544/252; 514/267

[56] References Cited

U.S. PATENT DOCUMENTS

| | | | |
|---|---|---|---|
| 3,876,788 | 4/1975 | Hodson et al. | 514/267 |
| 4,017,625 | 4/1977 | Kadin | 514/267 |
| 4,127,720 | 11/1978 | Juby et al. | 544/252 |
| 4,377,580 | 3/1983 | Ueda et al. | 514/267 |
| 4,460,771 | 7/1984 | Mészáros et al. | 544/282 |

FOREIGN PATENT DOCUMENTS 0143001  5/1985  European Pat. Off. ............ 544/252
0172472  9/1984  Japan ................................. 544/252
0172490  9/1984  Japan ................................. 544/252

OTHER PUBLICATIONS

Chemical Abstracts, vol. 102, 1985, p. 696, No. 113322z, Abstract.

*Primary Examiner*—Donald G. Daus
*Assistant Examiner*—Diana G. Rivers
*Attorney, Agent, or Firm*—Oblon, Fisher, Spivak, McClelland & Maier

[57] ABSTRACT

Pyrimidoisoquinoline/compounds of the formula:

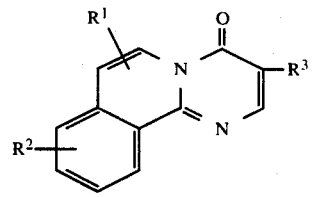

where $R^1$ is H, halogen or lower alkyl, $R^2$ is $NH_2$, $NO_2$ or acylamino and $R^3$ is carboxy or protected carboxy, pharmaceutically acceptable salts thereof, and pharmaceutical compositions thereof are disclosed in this application. Also disclosed is a method of treating allergies by administering the compounds of this invention.

10 Claims, No Drawings

PYRIMIDOISOQUINOLINE DERIVATIVES USEFUL FOR TREATING ALLERGIES

BACKGROUND OF THE INVENTION

Field of the Invention

This invention relates to new pyrimidoisoquinoline derivatives. More particularly, it relates to new pyrimidoisoquinoline derivatives and pharmaceutically acceptable salts thereof, to processes for preparation thereof, to a pharmaceutical composition comprising the same, and to a method of use of the same in treatment of symptoms associated with allergic manifestations, e.g. asthmatic conditions.

Summary of the Invention

This invention provides new pyrimidoisoquinoline derivatives which are useful as antiallergic agents.

This invention provides processes for preparing the pyrimidoisoquinoline derivatives.

This invention provides a pharmaceutical composition comprising the pyrimidoisoquinoline derivatives.

DESCRIPTION OF THE INVENTION

Pyrimidoisoquinoline derivatives of this invention can be represented by the following formula:

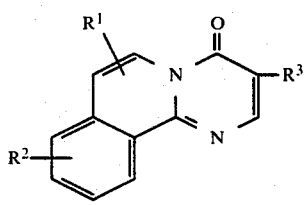

[I]

wherein
$R^1$ is hydrogen, halogen or lower alkyl,
$R^2$ is amino, nitro or acylamino and
$R^3$ is carboxy or protected carboxy,
and pharmaceutically acceptable salts thereof.

The pharmaceutically acceptable salts of pyrimidoisoquinoline derivatives (I) may include a salt with an inorganic or organic base (e.g. sodium salt, potassium salt, ethanolamine salt, tris(hydroxymethyl)-methylammonium salt, etc.) and an acid addition salt (e.g. hydrochloride, etc.).

According to this invention, the new pyrimidoisoquinoline derivatives (I) and pharmaceutically acceptable salts thereof can be prepared by, for example, the following processes.

Process 1:

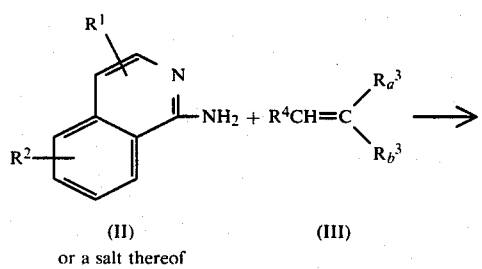

(II)
or a salt thereof (III)

Process 2:

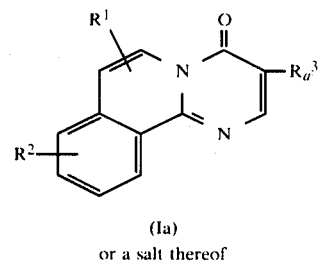

(Ia)
or a salt thereof

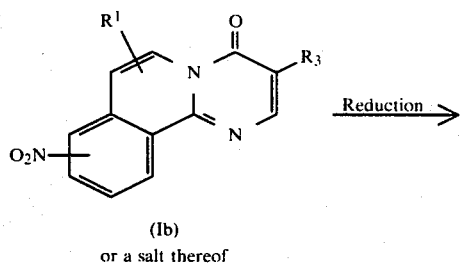

Reduction →

(Ib)
or a salt thereof

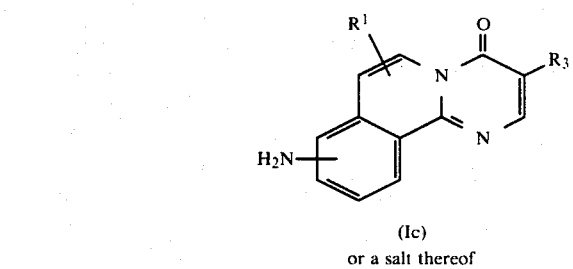

(Ic)
or a salt thereof

Process 3:

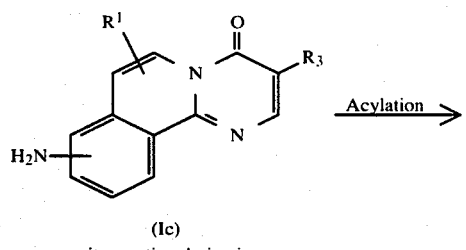

Acylation →

(Ic)
or its reactive derivative
at the amino group
or a salt thereof

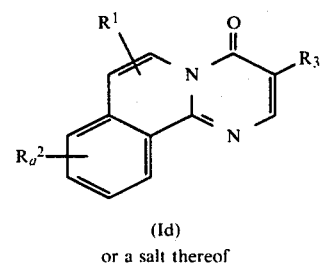

(Id)
or a salt thereof

Process 4:

-continued

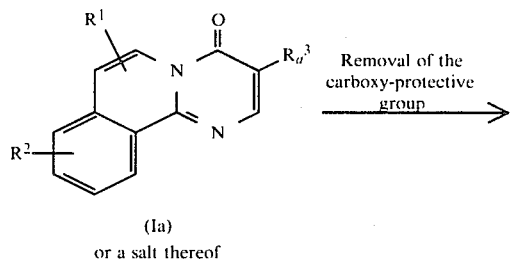

(Ia)
or a salt thereof

Removal of the carboxy-protective group →

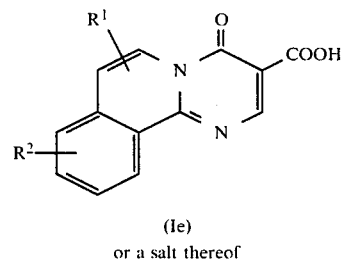

(Ie)
or a salt thereof

Process 5:

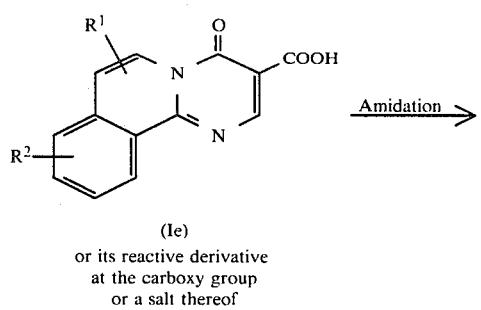

(Ie)
or its reactive derivative
at the carboxy group
or a salt thereof

Amidation →

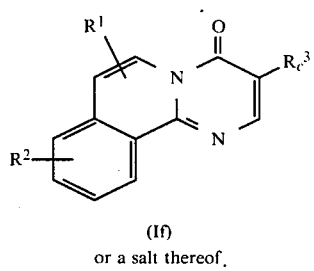

(If)
or a salt thereof.

Process 6:

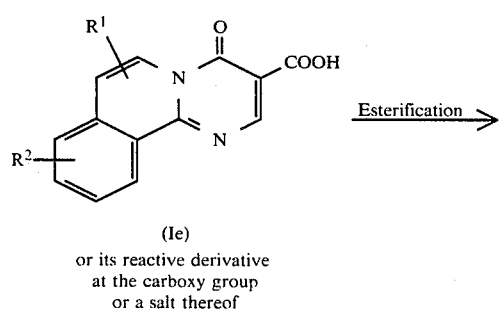

(Ie)
or its reactive derivative
at the carboxy group
or a salt thereof

Esterification →

-continued

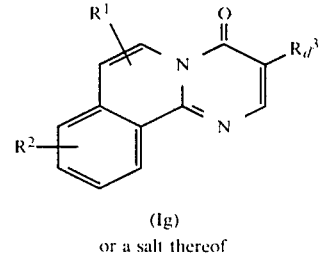

(Ig)
or a salt thereof wherein
$R^1$, $R^2$ and $R^3$ are each as defined above,
$R_a^2$ is acylamino,
$R_a^3$ and $R_b^3$ are each protected carboxy,
$R_c^3$ is an amidated carboxy,
$R_d^3$ is an esterified carboxy, and
$R^4$ is alkoxy.

The starting compound (II) or a salt thereof is a new compound and can be prepared by, for example, the preparation as illustrated below and in a similar manner thereto.

In the above and subsequent descriptions of this specification, suitable examples and illustrations of the various definitions are explained in detail in the following paragraphs.

The term "lower" is intended to mean 1 to 6 carbon atom(s), unless otherwise indicated.

The term "higher" is intended to mean more than 6 carbon atoms, and more preferably 7 to 20 carbon atoms.

"Halogen" may include fluorine, chlorine, bromine and iodine.

Suitable "lower alkyl" may include methyl, ethyl, propyl, isopropyl, butyl, isobutyl, t-butyl, pentyl, hexyl and the like.

Suitable "acyl" moiety in the term "acylamino" may include the residue of organic acid such as organic carboxylic acid, organic sulfonic acid, organic carbonic acid and the like.

Suitable "acyl" may be alkanoyl such as lower alkanoyl (e.g. formyl, acetyl, propionyl, butyryl, isobutyryl, 3,3-dimethylbutyryl, valeryl, isovaleryl, pivaloyl) or higher alkanoyl (e.g. heptanoyl, 2,3-dimethylpentanoyl, lauroyl, myristoyl, palmitoyl, stearoyl), lower cycloalkyl-carbonyl having 4 to 8 carbon atoms (e.g. cyclopentylcarbonyl, cyclohexylcarbonyl, cycloheptylcarbonyl), lower alkoxycarbonyl (e.g. methoxycarbonyl, ethoxycarbonyl, propoxycarbonyl), lower alkoxalyl having 3 to 9 carbon atoms (e.g. methoxalyl, ethoxalyl, propoxalyl), lower alkanesulfonyl (e.g. mesyl, ethanesulfonyl, propanesulfonyl), arylcarbamoyl (e.g. phenylcarbamoyl, tolylcarbamoyl) and the like.

The above exemplified acyl may have optionally one or more suitable substituent(s) such as hydroxy, acyloxy (e.g. lower alkanoyloxy), heterocyclic carboxamido (e.g. nicotinamido) and the like.

Suitable "protected carboxy" may include esterified carboxy and amidated carboxy, wherein suitable "esterified carboxy" may include lower alkoxycarbonyl which may have heterocyclic carboxamido (e.g. nicotinamido) such as methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, 2-nicotinamidoethoxycarbonyl, and the like.

Suitable "amidated carboxy" may include carbamoyl which may have suitable substituent(s) on the nitrogen atom, wherein said substituent(s) may include heterocyclic groups, heterocyclic(lower)alkyl groups and the like.

"Heterocyclic" in the "heterocyclic carboxamido", "heterocyclic group" and "heterocyclic(lower)alkyl group" as mentioned above means saturated or unsaturated, monocyclic or polycyclic heterocyclic group containing at least one hetero-atom such as an oxygen, sulfur, nitrogen atom and the like. And especially preferably "heterocyclic" may be heterocyclic group such as unsaturated 3 to 8-membered more preferably 5 or 6-membered heteromonocyclic group containing 1 to 4-nitrogen atom(s), for example, pyrrolyl, pyrrolinyl, pyrrolidinyl, piperazinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2-tetrazolyl, etc.), or the like.

The above exemplified "heterocyclic" may have optionally one or more suitable substituent(s) such as ar(lower)alkyl (e.g. diphenylmethyl, benzyl, etc.).

Preferable "amidated carboxy" may be N-tetrazolylcarbamoyl (e.g. N-1H-tetrazolylcarbamoyl, N-2H-tetrazolylcarbamoyl), 4-ar(lower)alkylpiperazin-1-yl(lower)alkylcarbamoyl [e.g. N-(4-diphenylmethylpiperazin-1-yl)ethylcarbamoyl, etc.].

Suitable "alkoxy" may include lower or higher alkoxy such as propoxy, isopropoxy, butoxy, isobutoxy, t-butoxy, pentyloxy, hexyloxy and the like.

Suitable examples of the $R^1$, $R^2$ and $R^3$ groups in the object compound (I) are those in which
$R^1$ is hydrogen, methyl or bromo,
$R^2$ is amino, nitro, pivaloylamino, isobutyrylamino, 2-hydroxypropionylamino, 2-acetoxypropionylamino, 3,3-dimethylbutyrylamino, 2,3-dimethylpentanoylamino, cyclohexylcarbonylamino, ethoxycarbonylamino, mesylamino, 3-(nicotinoylamino)propionylamino or phenylureido, and
$R^3$ is carboxy, ethoxycarbonyl, 2-nicotinamidoethoxycarbonyl, N-(1H-tetrazol-5-yl)carbamoyl or N-[2-(4-diphenylmethylpiperazin-1-yl)ethyl]carbamoyl.

The processes as illustrated above are explained in more detail in the following paragraphs.

PROCESS 1

The object compound (Ia) or a salt thereof can be prepared by reacting the compound (II) or a salt thereof with the compound (III).

The salt of the compound (II) is an acid addition salt (e.g. hydrochloride, sulfate, etc.).

This reaction is usually carried out in a solvent which does not adversely influence the reaction such as N,N-dimethylformamide, propanol, isobutyl alcohol, diphenylether, toluene, xylene and the like under heating.

PROCESS 2

The compound (Ic) or a salt thereof can be prepared by reducing the compound (Ib) or a salt thereof.

The reduction is carried out in a conventional manner such as a reduction using a reducing agent (e.g. combination of iron and ammonium chloride, etc.), catalytic reduction and the like.

The reduction is usually carried out in a solvent which does not adversely influence the reaction such as water, ethanol, propanol, isobutyl alcohol, N,N-dimethylformamide, tetrahydrofuran, chloroform and the like, at a temperature range of cooling to heating.

PROCESS 3

The compound (Id) or a salt thereof can be prepared by reacting the compound (Ic) or its reactive derivative at the amino group or a salt thereof with an acylating agent.

Suitable reactive derivative at the amino group of the compound (Ic) may include Schiff's base type imino or its tautomeric enamine type isomer formed by the reaction of the compound (Ic) with a carbonyl compound such as aldehyde, ketone or the like; a silyl derivative formed by the reaction of the compound (Ic) with a silyl compound such as bis(trimethylsilyl)acetamide, trimethylsilylacetamide or the like; a derivative formed by reaction of the compound (Ic) with phosphorus trichloride or phosgene, and the like.

The acylating agent to be used in this reaction includes an organic acid (i.e. $R_b{}^2$ OH (IV), in which $R_b{}^2$ is acyl) and its reactive derivative.

The suitable reactive derivative of the compound (IV) may be a conventional ones such as an acid halide (e.g. acid chloride, acid bromide, etc.), an acid azide an acid anhydride, an activated amide, an activated ester, an isocyanate and the like.

When free acid is used as an acylating agent, the acylation reaction may preferably be conducted in the presence of a conventional condensing agent.

The reaction is usually conducted in a solvent which does not adversely influence the reaction such as N,N-dimethylformamide, dimethylsulfoxide, tetrahydrofuran, dichloromethane, chloroform, pyridine or a mixture thereof.

The reaction can also be conducted preferably in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecen-5,etc.) and the like.

The reaction may preferably be conducted within the range of cooling to ambient temperature.

PROCESS 4

The compound (Ie) or a salt thereof can be prepared by subjecting the compound (Ia) or a salt thereof to removal reaction of the carboxy-protective group.

The removal reaction of this process may include hydrolysis, reduction and the like.

The hydrolysis is preferably carried out in the presence of inorganic or organic acid (e.g. hydrochloric acid, sulfuric acid, acetic acid, trifluoroacetic acid, etc.), or inorganic or organic base (e.g. sodium hydroxide, etc.).

The reaction of this process is usually carried out in a solvent which does not adversely influence the reaction such as water, methanol, ethanol, propanol, acetic acid and the like, at a temperature range of cooling to heating.

7

When the starting compound (Ia) has acylamino substituted by acyloxy for $R^2$, acyl group of said acyloxy may occasionally be removed off to transform into hydrogen together with removal of carboxy-protective group in this reaction. This case is also included within the scope of this invention.

PROCESS 5

The compound (If) or a salt thereof can be prepared by reacting the compound (Ie) or its reactive derivative at the carboxy group or a salt thereof with an amidating agent.

The amidating agent may include an amine (i.e. $R_e^3$ $NH_2$ (V), in which $R_e^3$ is a suitable substituent(s) such as heterocyclic group, ar(lower)alkyl heterocyclic(lower-)alkyl) and its reactive derivative or a salt thereof.

Suitable reactive derivative of the compound (Ie) may include an acid halide, an acid anhydride, an activated ester and the like.

Suitable reactive derivative of the compound (V) may be the same one as that of the compound (Ic).

This reaction is usually carried out in a solvent which does not adversely influence the reaction such as N,N-dimethylformamide, dimethylsulfoxide, pyridine, dichloromethane and the like.

The reaction temperature is not critical, and the reaction be carried out within the temperature range of cooling to heating.

This reaction is preferably carried out in the presence of a condensing agent (e.g. 1,1-carbonyldiimidazole, etc.).

PROCESS 6

The compound (Ig) or a salt thereof can be prepared by reacting the compound (Ie) or its reactive derivative at the carboxy group or a salt thereof with an esterifying agent.

The esterifying agent may include an alcohol (i.e. $R_f^3$ OH (VI), in which $R_f^3$ is a suitable substituent(s) such as lower alkyl which may have heterocyclic carboxamido) and its reactive derivative or a salt thereof.

Suitable reactive derivative of the compound (Ie) may include an acid halide, an acid anhydride, an activated ester and the like.

Suitable reactive derivative of the compound (VI) may include the corresponding halide (e.g. alkyl halide), diazocompound (e.g. diazoalkane), sulfonate (alkylsulfonate), sulfate or salt with an alkali metal or alkaline earth metal and the like.

This reaction is usually carried out in a solvent which does not adversely influence the reaction such as N,N-dimethylformamide, dimethylsulfoxide, pyridine, dichloromethane and the like.

The reaction temperature is not critical, and the reaction may be carried out within the temperature range of cooling to heating.

The object compounds of the above processes 1–6 can be purified and converted to the desired salt in a conventional manner.

The object compound (I) of this invention and pharmaceutically acceptable salt thereof possess strong antiallergic activity. Accordingly, the object compound of this invention is useful for the treatment of symptoms associated with allergic diseases such as allergic asthma, allergic rhinitis, urticaria, pollenosis, allergic conjuctivitis, atopic dermatitis, ulcerative colitis, alimentary allergy (e.g. milk allergy), bird fancier's disease, aphthous stomatitis and the like. For illustrating purpose, the antiallergic activity of some representative compounds of the object compound (I) are shown in the following.

TEST I [Inhibitory effect on PCA (Passive Cutaneous Anaphylaxis) reaction]

(1) Test compound (a) Test compound of the formula:

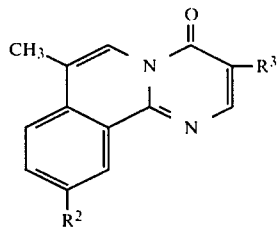

| Test compound No. | $R^2$ | $R^3$ |
|---|---|---|
| 1 | $-NH_2$ | $-COOC_2H_5$ |
| 2 | $-NH_2$ | $-COOH$ |
| 3 | $-NO_2$ | $-COOH$ |
| 4 | $-NHCOCHCH_2H_5$<br>$\quad\ \|\quad\ \backslash$<br>$\quad CH_3\ \ CH_3$ | $-COOC_2H_5$ |
| 5 | $-NHCOCHCH_2H_5$<br>$\quad\ \|\quad\ \backslash$<br>$\quad CH_3\ \ CH_3$ | $-CONH-\underset{H}{\underset{\|}{\overset{N-N}{\underset{N-N}{\|}}}}$ |
| 6 | $\quad\ CH_3$<br>$\quad\ \|$<br>$-NHCOCHCH_3$ | $-COOC_2H_5$ |
| 7 | $-NHCO-\bigcirc$ | $-COOC_2H_5$ |
| 8 | $\quad\ CH_3$<br>$\quad\ \|$<br>$-NHCOCHCH_3$ | $-COOH$ |
| 9 | $-NO_2$ | $-COONa$ |
| 10 | $-NHCOCHCH_2H_5$<br>$\quad\ \|\quad\ \backslash$<br>$\quad CH_3\ \ CH_3$ | $-COONa$ |
| 11 | $-NHCOOC_2H_5$ | $-COOC_2H_5$ |
| 12 | $-NHSO_2CH_3$ | $-COOH$ |
| 13 | $-NHCOCH_2C(CH_3)_3$ | $-COOH$ |
| 14 | $\quad\ OH$<br>$\quad\ \|$<br>$-NHCOCH-CH_3$ | $-COOH$ |
| 15 | $-NHCO-\bigcirc$ | $-COOH$ |
| 16 | $-NHCOC(CH_3)_3$ | $-COOH$ |
| 17 | $-NHCOCHCH_2H_5$<br>$\quad\ \|\quad\ \backslash$<br>$\quad CH_3\ \ CH_3$ | $-COOH$ |

(b) Test compound of the formula:

[Structure: pyrimidoisoquinoline with substituents $R^2$ and $R^3$]

| Test Compound No. | $R^2$ | $R^3$ |
|---|---|---|
| 18 | —NHCOCH(CH₃)CHC₂H₅ | —COO(CH₂)₂NHCO-(3-pyridyl) |
| 19 | —NHCOCH(CH₃)CHC₂H₅ | —COOH |

(2) Test Method

(a) Preparation of antiserum

A solution of egg albumin (2 mg) in B. pertussisdiphtheria-tetanus mixed vaccine (1 ml) was mixed with Freund incomplete adjuvant (1 ml) to give an emulsion. The emulsion was given subcutaneously in a single dose of 1 ml divided equally (0.25 ml) to the four foot pads of male SD (Spraque-Dawley) strain rats aged 8 weeks, each weighing about 300 g.

8 days after the immunization, blood samples were collected from femoral artery of the rats and allowed to stand under ice-cooling for 5 hours. The separated supernatant was centrifuged at 4° C. (10,000 r.p.m.×1 hour). The antisera thus obtained were stored at −80° C. prior to use.

(b) Inhibitory effect on P.C.A.

Male SD-strain rats aged 8 weeks, weighing 250 to 300 g, were used for PCA reaction with the homologous reaginic antiserum as prepared above. Each 0.1 ml of 32 fold diluted antiserum were injected intradermally at separate sites on the back of rats clipped free of hair, and 48 hours later, 1 ml of aqueous solution containing each 5 mg of the egg albumin and Evans blue was injected intravenously to evoke PCA reaction. Test compound was given to the animals intravenously 5 minutes before the challenge with antigen. Control group received vehicle. Each dose group consisted of 4 animals. One hour after the challenge with antigen, the animals were sacrificed and then skinned. Dye spots caused with antiserum were investigated for their size on the reversed side of the skin, respectively. The results were expressed by percent inhibition values calculated from averaged values of the longest and shortest diameters for each spot in comparison with those in control group.

(3) Test Results

Test results are shown in the following table. (Dosage of the test compound: 1 mg/kg)

| Test Compound No. | Inhibitory effect (%) |
|---|---|
| 1 | 100 |
| 2 | 100 |
| 3 | 84.9 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 17 | 100 |
| 18 | 100 |
| 19 | 100 |

The pyrimidoisoquinoline derivatives (I) of this invention can be used as an active antiallergic agent either in free form or in the form of the pharmaceutically acceptable salt such as a salt with inorganic or organic acid, a salt with inorganic or organic base and a salt with an amino acid.

The object compound (I) or its pharmaceutically acceptable salt can usually be administered to mammals including human beings in the form of a conventional pharmaceutical composition such as capsule, microcapsule, tablet, granule, powder, troche, syrup, aerosol, inhalation, solution, injection, suspension, emulsion, suppository, ointment, or the like.

The pharmaceutical composition of this invention may contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The dose of the present active ingredient is to be varied depending on various factors such as weight and/or age of a patient and/or a stage of the allergic disease, and further the kind of administration route. In general, an effective dose may be in a range of about 20–2000 mg/day for an oral route, about 2.5–250 mg/day for an intramuscular or intravenous injection, about 10–1000 mg/day for a subcutaneous injection and about 120 mg–2000 mg/day for a rectal route. The total daily amount mentioned above may be divisionally given to the patient at intervals of 6–12 hours per day. A preferable single dose of the present active ingredient may be, for example, about 10–500 mg per tablet or capsule, about 1.25-250 mg per vial or ampoule, or about 60-500 mg per suppository, and so on, and further a pharmaceutical form for an external use may be, for example, about 1-10% ointment, solution or emulsion, etc.

Starting compounds to be used in the preparation of the pyrimidoisoquinoline derivatives (I) of this invention can be specifically prepared in the following manner.

PREPARATION 1

(1) To a stirred solution of potassium nitrate (10 g) in conc-sulfuric acid (50 ml) was added slowly a solution of 3,4-dihydro-4-methylisoquinoline (12 g) in conc-sulfuric acid (50 ml) at $-20° \sim -10°$ C. over a period of an hour. The reaction mixture was allowed to stir at ambient temperature for 3 hours and heated at 60° C. for 1.5 hours. The reaction mixture was poured onto ice, and adjusted to alkaline pH with 28% ammonium hydroxide under cooling. The resulting brown solid was filtered off, washed with water, and dried in vacuo to give 3,4-dihydro-4-methyl-7-nitroisoquinoline (14.63 g).

IR (Nujol): 1628, 1504, 1342, 772, 744 cm$^{-1}$.

NMR (CDCl$_3$, δ): 1.33 (3H, d, J=8.0 Hz), 3.02 (1H, m), 3.80 (2H, m), 7.46 (1H, d, J=8.8 Hz), 8.17 (1H, d, J=2.8 Hz), 8.29 (1H, dd, J=8.8 and 2.8 Hz), 8.46 (1H, s).

Mass: 190 (M+) 143, 115.

(2) A mixture of 3,4-dihydro-4-methyl-7-nitroisoquinoline (14.63 g) and palladium black (4 g) in decahydronaphthalene (170 ml) was refluxed for 6 hours with stirring. The reaction mixture was allowed to stand overnight at ambient temperature, and then filtered and the residue on a filter was washed with chloroform. The filtrate was extracted with 2N hydrochloric acid (70 ml×3). Aqueous sodium hydroxide was added slowly to the combined aqueous layer, under dryice-acetone cooling. The light brown solid was collected, washed with water and dried. The crude product was chromatographed on silica gel column using chloroform as an eluent to give 4-methyl-7-nitroisoquinoline (6.06 g).

IR (Nujol): 1620, 1460, 1340, 795 cm$^{-1}$.

NMR (CDCl$_3$, δ): 2.70 (3H, s), 8.13 (1H, d, J=9,6 Hz), 8.49 (1H, dd, J=9,6, 2,4 Hz), 8.59 (1H, s), 8.91 (1H, d, J=2,4 Hz), 9.32 (1H, s)

MASS: 188 (M+), 142, 115

(3) A solution of 4-methyl-7-nitroisoquinoline (400 mg), and 30% hydrogen peroxide (0.65 ml) in acetic acid (2 ml) was refluxed for 3.5 hours. After removal of the solvent, the residue in ether (50 ml) was stirred to give yellow powder. The powder was collected and washed with ether and dried to give 4-methyl-7-nitroisoquinoline N-oxide (360 mg).

IR (Nujol): 3060, 1602, 1524, 1461, 1344, 1179 cm$^{-1}$

NMR (DMSO-d$_6$, δ): 2.60 (3H, s), 8.0-8.5 (3H, m), 8.88 (1H, s), 9.10 (1H, s)

MASS: 204 (M+)

(4) To a suspension of 4-methyl-7-nitroisoquinoline N-oxide (0.85 g) in pyridine (20 ml) was added 0.32 g each of tosyl chloride for three times under ice cooling. After stirring overnight at ambient temperature, the reaction mixture was concentrated in vacuo. To the resulting residue was added ethanolamine (18 ml) at ambient temperature and the mixture was stirred for 45 hours. The reaction mixture was poured into ice-water to precipitate crude 1-amino-4-methyl-7-nitroisoquinoline (0.51 g).

IR (Nujol): 3460, 3310, 3360, 3100, 1612, 1329 cm$^{-1}$.

NMR (DMSO-d$_6$, δ): 2.34 (3H, s), 7.20 (2H, s), 7.90 (1H, s), 7.96 (1H, d, J=10.0 Hz), 8.39 (1H, dd, J=10.0 and 2.0 Hz), 9.27 (1H, d, J=2.0 Hz).

MASS: 203 (M+).

PREPARATION 2

The following compound was obtained according to a similar procedure to that of Preparation 1(4).

1-Amino-7-nitroisoquinoline.

IR(Nujol): 3460, 3320, 3090, 1500, 1325, 839 cm$^{-1}$.

NMR (DMSO-d$_6$, δ): 7.01 (1H, d, J=6.0 Hz), 7.37 (2H, brs), 7.85 (1H, d, J=9.0 Hz), 8.01 (1H, d, J=6.0 Hz), 8.31 (1H, dd, J=9.0 and 2.2 Hz), 9.27 (1H, d, J=2.2 Hz).

MASS: 189 (M+), 143, 116.

PREPARATION 3

The following compound was obtained according to a similar procedure to that of Preparation 1(4).

1-Amino-5-nitroisoquinoline.

IR (Nujol): 3480, 3300, 3105, 1640, 1510, 1332, 790 cm$^{-1}$.

NMR (DMSO-d$_6$, δ): 7.27 (2H, s), 7.34 (1H, d, J=6 Hz), 7.65 (1H, d, J=8.1 Hz), 8.05 (1H, d, J=6.0 Hz), 8.44 (1H, d, J=8.1 Hz), 8.67 (1H, d, J=8.1 Hz).

MASS: 189 (M+).

PREPARATION 4

The following compound was obtained according to a similar procedure to that of Preparation 1(4).

1-Amino-5-bromo-8-nitroisoquinoline.

IR (Nujol): 3475, 3310, 1643, 1597, 1095, 865, 840, 740 cm$^{-1}$.

NMR (DMSO-d$_6$, δ): 6.35 (2H, s), 7.33 (1H, d, J=6.0 Hz), 7.87 (1H, d, J=8.0 Hz), 8.19 (1H, d, J=8.0 Hz), 8.21 (1H, d, J=6.0 Hz)

MASS: 269 (M++2), 268, 267 (M+), 250, 221, 142

The following examples are given for the purpose of illustrating this invention.

EXAMPLES

Example 1

A mixture of 1-amino-4-methyl-7-nitroisoquinoline (3.87 g), diethyl ethoxymethylenemalonate (4.53 g) in N,N-dimethylformamide (20 ml) was heated at 120° C. with stirring for 4 hours. Additional diethyl ethoxymethylenemalonate (1 g) was added to the mixture, and then the reaction mixture was refluxed for 18 hours and cooled to give precipitate. The crystals obtained were filtered off and washed with cold ethanol to give ethyl 7-methyl-10-nitro-4-oxo-4H-pyrimido[2,1-a]isoquinoline-3-carboxylate (4.21 g).

IR (Nujol): 1730, 1480, 1336, 1134 cm$^{-1}$.

MASS: 327 (M+), 282, 255, 227.

Example 2

A suspension of ethyl 7-methyl-10-nitro-4-oxo-4H-pyrimido[2,1-a]isoquinoline-3-carboxylate (260 mg) in a mixture of acetic acid (6 ml) and 36% hydrochloric acid (3 ml) was refluxed for 50 minutes. The mixture was cooled to 0° C. to give yellow solid. The yellow solid was collected and dried to give 7-methyl-10-nitro-4-oxo-4H-pyrimido[2,1-a]isoquinoline-3-carboxylic acid (180 mg).

mp 301°~303° C.

IR (Nujol): 1748, 1498, 1343 cm$^{-1}$.

MASS: 299 (M+), 255, 227.

Example 3

To a stirred mixture of ethyl 7-methyl-10-nitro-4-oxo-4H-pyrimido[2,1-a]isoquinoline-3-carboxylate (140 mg) and iron powder (90 mg) in a mixture of water (0.5 ml) and ethanol (13 ml) was added a solution of ammonium chloride (90 mg) in water (0.5 ml) under refluxing. After refluxing for 1 hour and 50 minutes, ammonium chloride (28 mg) in water (0.5 ml) and iron (50 mg) was added, and then the mixture was stirred for additional 1 hour. The reaction mixture was filtered and the residue on a filter was washed with hot ethanol. The filtrate was concentrated in vacuo and then treated with dilute sodium hydrogen carbonate solution to give crude product. Chromatography on silica gel with chloroform-methanol gave pure ethyl 10-amino-7-methyl-4-oxo-4H-pyrimido[2,1-a]isoquinoline-3-carboxylate (100 mg).

m.p. 245°~248° C. (CHCl$_3$—MeOH).

IR (Nujol): 3440, 3350, 3230, 1698, 1678, 1480, 1290, 1136 cm$^{-1}$.

NMR (DMSO-d$_6$, δ): 1.34 (3H, t, J=6.4 Hz), 2.49 (3H, s), 4.32 (2H, q, J=6.4 Hz), 6.05 (2H, s), 7.28 (1H, dd, J=8.2 and 2.2 Hz), 7.72 (1H, d, J=8.2 Hz), 8.04 (1H, d, J=2.2 Hz), 8.33 (1H, s), 8.78 (1H, s)

MASS: 297 (M+), 252, 225, 197, 157.

Example 4

A suspension of ethyl 10-amino-7-methyl-4-oxo-4H-pyrimido[2,1-a]isoquinoline-3-carboxylate (400 mg) in a mixture of acetic acid (6 ml) and 36% hydrochloric acid (3 ml) was refluxed for 55 minutes. The mixture was cooled and diluted with water. The precipitated solid obtained was collected and dissolved into 6 ml of 1N aqueous sodium hydroxide. The resulting solution was filtered for removal of insoluble materials. The filtrate obtained was cooled and adjusted to pH 6 with 1N hydrochloric acid and neutralized with acetic acid to give 10-amino-7-methyl-4-oxo-4H-pyrimido[2,1-a]isoquinoline-3-carboxylic acid (270 mg).

mp>300° C.

IR (Nujol): 3455, 3340, 3200, 1726, 1613, 1456 cm$^{-1}$.

NMR (D$_2$O—NaOH, δ): 1.62 (3H, s), 6.3–6.6 (3H, m), 7.10 (1H, s), 8.07 (1H, s).

MASS: 269 (M+), 225, 197, 157

Example 5

To a solution of ethyl 10-amino-7-methyl-4-oxo-4H-pyrimido[2,1-a]isoquinoline-3-carboxylate (1.5 g) in pyridine (110 ml) was added 2,3-dimethylpentanoyl chloride (1.4 g) under ice cooling. After stirring for 2 hours at ambient temperature, the reaction mixture was concentrated in vacuo. The residue in chloroform (100 ml) was washed with water, a cold 1N hydrochloric acid and water in turn and dried over magnesium sulfate. After removal of the solvent, the residue was chromatographed on a silica gel column using chloroform as an eluent to give ethyl 10-(2,3-dimethylpentanoylamino)-7-methyl-4-oxo-4H-pyrimido[2,1-a]isoquinoline-3-carboxylate (1.94 g).

m.p. 216°~218° C. (CHCl$_3$—EtOH).

IR (Nujol): 3250, 3100, 1755, 1742, 1653, 1490, 1122 cm$^{-1}$.

NMR (CDCl$_3$, δ): 0.7–2.5 (16H, m), 2.57 (3H, s), 4.43 (2H, q, J=7.2 Hz), 7.79 (1H, d, J=8.2 Hz), 8.00 (1H, s), 8.50 (1H, dd, J=8.2 and 2.2 Hz), 8.66 (1H, s), 8.90 (1H, d, J=2.2 Hz), 8.97 (1H, s).

Example 6

A mixture of ethyl 10-(2,3-dimethylpentanoylamino)-7methyl-4-oxo-4H-pyrimido[2,1-a]isoquinoline-3-carboxylate (500 mg) and 1N sodium hydroxide (3.6 ml) in methanol (20 ml) was stirred at ambient temperature for 40 hours.

The reaction mixture was diluted with water (30 ml) and filtered off. The filtrate was acidified with 1N hydrochloric acid, and the resultant precipitate was collected and dried to give 10-(2,3-dimethylpentanoylamino)-7-methyl-4-oxo-4H-pyrimido[2,1-a]isoquinoline-3-carboxylic acid (320 mg).

IR (Nujol): 3320, 1743, 1690, 1515, 1500, 1433 cm$^{-1}$.

NMR (DMSO-d$_6$, δ): 0.7–2.4 (13H, m), 2.62 (3H, s), 8.02 (1H, d, J=8,4 Hz), 8.26 (1H, dd, J=8.4 and 2.4 Hz), 8.59 (1H, s), 8.97 (1H, s), 9.38 (1H, d, J=2.4 Hz), 10.37 (1H, s), 12.3–13.0 (1H, m).

MASS: 381 (M+), 337, 309, 269, 251, 197, 85.

Example 7

The following compound was obtained according to a similar procedure to that of Example 5.

Ethyl 10-pivaloylamino-7-methyl-4-oxo-4H-pyrimido[2,1-a]isoquinoline-3-carboxylate.

IR (Nujol): 3410, 3370, 1740, 1288, 1322, 800 cm$^{-1}$.

NMR (CDCl$_3$, δ): 1.42 (9H, s), 1.45 (3H, t, J=7.0 Hz), 2.56 (3H, s), 4.44 (2H, q, J=7.0 Hz), 7.79 (1H, d, J=9.0 Hz), 8.00 (1H, broads), 8.48 (1H, dd, J=9.0 and 2.2 Hz), 8.65 (1H, s), 8.85 (1H, d, J=2.2 Hz), 8.94 (1H, s).

Example 8

A mixture of ethyl 10-pivaloylamino-7-methyl-4-oxo-4H-pyrimido[2,1-a]isoquinoline-3-carboxylate (400 mg) and 1N sodium hydroxide (3.1 ml) in aqueous methanol (19 ml) was stirred at ambient temperature for 2 days. Aqueous methanol was added to the reaction mixture and then heated on a water bath until almost all the precipitate was dissolved. The solution was filtered, and the filtrate was acidified with 1N hydrochloric acid. The resultant precipitate was collected, washed successively with water and methanol, and dried. Recrystallization from a mixture of N,N-dimethylformamide and water gave pure 10-pivaloylamino-7-methyl-4-oxo-4H-pyrimido[2,1-a]isoquinoline-3-carboxylic acid (0.31 g).

IR (Nujol): 3350, 1730, 1687, 1493, 1430, 1292, 853, 805 cm$^{-1}$.

MASS: 353 (M+), 309, 281, 251, 224, 197, 157, 57.

Example 9

The following compound was obtained according to a similar procedure to that of Example 5.

Ethyl 10-cyclohexyl-carbonylamino-7-methyl-4-oxo-4H-pyrimido[2,1-a]isoquinoline-3-carboxylate.

IR (Nujol): 3340, 1707, 1690, 1679, 1480, 797 cm$^{-1}$.

NMR (DMSO-d$_6$, δ): 1.1–2.8 (11H, m), 1.35 (3H, t, J=7.4 Hz), 2.53 (3H, s), 4.33 (2H, q, J=7.4 Hz), 7.87 (1H, d, J=8.8 Hz), 8.18 (1H, dd, J=8.8 and 2.0 Hz), 8.51 (1H, s), 8.80 (1H, s), 9.21 (1H, d, J=2.0 Hz), 10.30 (1H, s).

Example 10

The following compound was obtained according to a similar manner to that of Example 5.

Ethyl 10-isobutyrylamino-7-methyl-4-oxo-4H-pyrimido[2,1-a]isoquinoline-3-carboxylate.

NMR (DMSO-d₆, δ): 1.17 (6H, d, J=6.6 Hz), 1.32 (3H, t, J=7.2 Hz), 2.3-2.9 (1H, m), 2.52 (3H, s), 4.30 (2H, q, J=7.2 Hz), 7.87 (1H, d, J=8.2 Hz), 8.21 (1H, dd, J=8.2 and 2.2 Hz), 8.49 (1H, s), 8.79 (1H, s), 9.18 (1H, d, J=2.2 Hz), 10.31 (1H, s).

Example 11

To a stirred suspension in 10-(2,3-dimethylpentanoylamino)-7-methyl-4-oxo-4H-pyrimido[2,1-a]isoquinoline-3-carboxylic acid (257 mg) in N,N-dimethylformamide (3.5 ml) was added 1,1'-carbonyldiimidazole (142 mg) at ambient temperature under an inert atmosphere and then heated at 100° C. To the mixture was added 5-amino-1H-tetrazol (75 mg), heated for 1 hour at the same temperature, and cooled.

The resultant precipitate was collected by filtration, washed successively with N,N'-dimethylformamide and methanol, and dried to give N-(1H-tetrazol-5-yl)-10-(2,3-dimethylpentanoylamino)-7-methyl-4-oxo-4H-pyrimido[2,1-a]isoquinoline-3-carboxamide (0.16 g).
mp: >300° C.
IR (Nujol): 3500, 3290, 3100, 1682, 1597, 1470, 800 cm⁻¹.
MASS: 448 (M⁺), 420, 364, 337, 266, 251, 197, 157, 113, 85, 43.

Example 12

The following compound was obtained according to a similar procedure to that of Example 8.
10-Isobutyrylamino-7-methyl-4-oxo-4H-pyrimido[2,1-a]isoquinoline-3-carboxylic acid.
mp: >300° C.
IR (Nujol): 3310, 1743, 1550, 1466, 1440 cm⁻¹.
MASS: 339 (M⁺), 295, 269, 251, 225, 197, 157, 142, 115, 71, 43, 27.

Example 13

The following compound was obtained according to a similar procedure to that of Example 8.
10-Cyclohexyl-carbonylamino-7-methyl-4-oxo-4H-pyrimido[2,1-a]isoquinoline-3-carboxylic acid.
mp: >300° C.
IR (Nujol): 3310, 1743, 1693, 1496, 1436, 1073 cm⁻¹.
MASS: 379 (M⁺), 339, 307, 269, 251, 225, 197, 83, 55.

Example 14

A solution of 7-methyl-10-nitro-4-oxo-4H-pyrimido[2,1-a]isoquinoline-3-carboxylic acid (300 mg) in N,N-dimethylformamide (40 ml) was added to an aqueous sodium bicarbonate solution (60 ml). After being stirred for 1 hour, the mixture was allowed to stand in a refrigerator and the resultant precipitate was collected by filtration. To the solid was added aqueous methanol, stirred at room temperature, and collected by suction to give sodium 7-methyl-10-nitro-4-oxo-4H-pyrimido[2,1-a]isoquinoline-3-carboxylate (0.29 g).
mp: >300° C.
IR (Nujol): 3370 (br), 1707, 1497, 1342, 811 cm⁻¹.

Example 15

A mixture of ethyl 10-(2,3-dimethylpentanoylamino)-7-methyl-4-oxo-4H-pyrimido[2,1-a]isoquinoline-3-carboxylate (520 mg) and 1N aqueous sodium hydroxide (3.6 ml) in aqueous methanol (25 ml) was stirred at room temperature for 2 days. Methanol was added to the reaction mixture until nearly all the precipitate was dissolved. The solution was concentrated to a half volume under reduced pressure and then filtered. The filtrate was diluted with water and allowed to stand in a refrigerator. The resultant precipitate was collected, washed with water and dried to give sodium 10-(2,3-dimethylpentanoylamino)-7-methyl-4-oxo-4H-pyrimido[2,1-a]isoquinoline-3-carboxylate (210 mg).
mp: >300° C.
IR (Nujol): 3420, 3270, 1700, 1690, 1662, 1490, 1380, 817 cm⁻¹.

Example 16

To a solution oe ethyl 10-amino-7-methyl-4-oxo-4H-pyrimido[2,1-a]isoquinoline-3-carboxylate (800 mg) in pyridine (60 ml) was added mesyl chloride (0.28 ml) at ice bath temperature. The reaction mixture was allowed to stir overnight at room temperature and then concentrated in vacuo. The residue was collected, washed successively with 0.1N hydrochloric acid and water and recrystallized from N,N-dimethylformamide to give ethyl 10-mesylamino-7-methyl-4-oxo-4H-pyrimido[2,1-a]isoquinoline-3-carboxylate (0.76 g).
IR (Nujol): .3240, 1710, 1660, 1483, 1142, 962, 802 cm⁻¹.
MASS: 375 (M⁺), 360, 330, 296, 268, 251, 224, 196, 157, 128, 115, 79, 53, 29.

Example 17

The following compound was obtained according to a similar procedure to that of Example 16.
Ethyl 10-ethoxycarbonylamino-7-methyl-4-oxo-4H-pyrimido[2,1-a]isoquinoline-3-carboxylate.
mp 289°–292° C.
IR (Nujol): 3320, 1723, 1476, 1292, 1222, 1143, 1060, 803 cm⁻¹.
MASS: 369 (M⁺), 323, 297, 278, 251, 223, 183, 155, 140, 114, 78, 53, 29.

Example 18

The following compound was obtained according to a similar procedure to that of Example 8.
10-Mesylamino-7-methyl-4-oxo-4H-pyrimido[2,1-a]isoquinoline-3-carboxylic acid.
mp >300° C.
IR (Nujol): 3260, 3180, 1728, 1512, 1162, 1142, 802 cm⁻¹.
MASS: 347 (M⁺), 303, 275, 235, 224, 196, 169, 128, 115, 82, 53, 15.

Example 19

The following compound was obtained according to a similar procedure to that of Example 16.
Ethyl 10-ethoxalylamino-7-methyl-4-oxo-4H-pyrimido[2,1-a]isoquinoline-3-carboxylate.
mp 273°–275° C.
IR (Nujol): 3320, 1740, 1707, 1480, 1118, 800 cm⁻¹.
MASS: 397 (M⁺), 352, 325, 296, 278, 251, 223, 183, 157, 140, 115, 77, 53, 29.

Example 20

To a solution of ethyl 10-amino-7-methyl-4-oxo-4H-pyrimido[2,1-a]isoquinoline-3-carboxylate (600 mg) in pyridine (60 ml) was added phenyl isocyanate (0.22 ml) at ice bath temperature. The reaction mixture was allowed to stir overnight at room temperature. The precipitate was collected, washed with methanol and dried. Recrystallization from dimethyl sulfoxide gave ethyl 10-(3-phenylureido)-7-methyl-4-oxo-4H-pyrimido[2,1-a]isoquinoline-3-carboxylate (0.58 g).
mp >300° C.

IR (Nujol): 3350, 1727, 1704, 1482, 1216, 1138, 798 cm$^{-1}$.

MASS: 416 (M+), 323, 297, 252, 197, 157, 119, 64, 39.

Example 21

The following compound was obtained according to a similar procedure to that of Example 1.

Ethyl 10-nitro-4-oxo-4H-pyrimido[2,1-a]isoquinoline-3-carboxylate.

IR (Nujol): 3060, 1733, 1488, 1350, 1140, 803

NMR (CDCl$_3$, δ): 143 (3H, t, J=7.5 Hz), 4.47 (2H, q, J=7.5 Hz), 7.54 (1H, d, J=7.95 Hz), 8.02 (1H, d, J=9.0 Hz), 8.72 (1H, dd, J=9.0 and 3.0 Hz), 9.13 (1H, d, J=7.95 Hz), 9.14 (1H, s), 10.0 (1H, d, J=3.0 Hz)

MASS: 313 (M+), 268, 241, 173, 127, 29.

Example 22

The following compound was obtained according to a similar procedure to that of Example 3.

Ethyl 10-amino-4-oxo-4H-pyrimido[2,1-a]isoquinoline-3-carboxylate.

IR (Nujol): 3450, 3310, 3200, 3100, 1728, 1665, 1113, 830, 803, 780 cm$^{-1}$.

NMR (DMSO-d$_6$, δ): 1.32 (3H, t, J=6.8 Hz), 4.30 (2H, q, J=6.8 Hz), 6.09 (2H, br s), 7.30 (1H, dd, J=8.4 and 2.0 Hz), 7.55 (1H, d, J=7.2 Hz), 7.75 (1H, d, J=8.4 Hz), 8.03 (1H, d, J=2.0 Hz), 8.53 (1H, d, J=7.2 Hz), 8.86 (1H, s).

Example 23

The following compound was obtained according to a similar procedure to that of Example 5.

Ethyl 10-(2,3-dimethylpentanoylamino)-4-oxo-4H-pyrimido[2,1-a]isoquinoline-3-carboxylate.

IR (Nujol): 3350, 1720, 1680, 1483, 1305, 1118, 834 cm$^{-1}$.

NMR (CDCl$_3$, δ): 0.6–2.7 (16H, m), 4.44 (2H, q, J=7.4 Hz), 7.33 (1H, d, J=7.8 Hz), 7.72 (1H, d, J=9.0 Hz), 8.33 (1H, s), 8.47 (1H, dd, J=9.0 and 2.0 Hz), 8.81 (1H, d, J=7.8 Hz), 8.95 (1H, d, J=2.0 Hz), 9.00 (1H, s)

Example 24

The following compound was obtained according to a similar procedure to that of Example 8.

10-(2,3-Dimethylpentanoylamino)-4-oxo-4H-pyrimido[2,1-a]isoquinoline-3-carboxylic acid.

mp: >300° C.

IR (Nujol): 3320, 1740, 1492, 1122, 840 cm$^{-1}$.

MASS: 367 (M+), 255, 211, 183, 85, 43.

Example 25

The following compound was obtained according to a similar procedure to that of Example 1.

Ethyl 8-nitro-4-oxo-4H-pyrimido[2,1-a]isoquinoline-3-carboxylate.

mp: 202° C.

IR (Nujol): 1710, 1690, 1490, 1140, 790 cm$^{-1}$.

NMR (CDCl$_3$, δ): 1.44 (3H, t, J=6.6 Hz), 4.47 (2H, q, J=6.6 Hz), 7.87 (1H, t, J=8.0 Hz), 8.22 (1H, d, J=8.2 Hz), 8.62 (1H, d, J=8.0 Hz), 9.06 (1H, d, J=8.2 Hz), 9.07 (1H, s), 9.50 (1H, d, J=8.0 Hz)

Example 26

A suspension of ethyl 8-nitro-4-oxo-4H-pyrimido[2,1-a]isoquinoline-3-carboxylate (400 mg) in a mixture of acetic acid (20 ml) and 36% hydrochloric acid (4 ml) was heated at 80° C. for 5 hours. The mixture was cooled and diluted with water. The precipitated solid obtained was collected and dried to give 8-nitro-4-oxo-4H-pyrimido[2,1-a]isoquinoline-3-carboxylic acid (320 mg).

mp: >300° C. (Recrystallization from N,N'-dimethylformamide).

IR (Nujol): 1720, 1640, 1250, 880, 770 cm$^{-1}$.

MASS: 285 (M+), 241, 127, 53, 18.

Example 27

The following compound was obtained according to a similar procedure to that of Example 3.

Ethyl 8-amino-4-oxo-4H-pyrimido[2,1-a]isoquinoline-3-carboxylate mp: 225° C.

IR (Nujol): 3450, 3360, 1735, 1490, 1130 cm$^{-1}$.

NMR (CDCl$_3$, δ): 1.44 (1H, t, J=7.3 Hz), 4.47 (1H, q, J=7.3 Hz), 7.20 (1H, d, J=7.8 Hz), 7.48 (1H, d, J=7.8 Hz), 7.61 (1H, t, J=7.8 Hz), 8.58 (1H, d, J=7.8 Hz), 8.96 (1H, d, J=7.8 Hz), 9.11 (1H, s).

Example 28

The following compound was obtained according to a similar procedure to that of Example 4.

8-Amino-4-oxo-4H-pyrimido[2,1-a]isoquinoline-3-carboxylic acid.

mp: >300° C.

IR (Nujol): 3450, 3350, 1735, 1630, 1140, 787 cm$^{-1}$.

MASS: 255 (M+), 183, 143, 18.

Example 29

The following compound was obtained according to a similar procedure to that of Example 5.

Ethyl 8-(2,3-dimethylpentanoylamino)-4-oxo-4H-pyrimido[2,1-a]isoquinoline-3-carboxylate.

mp: 209°–210° C.

IR (Nujol): 3250, 3100, 1738, 1650, 1290, 1118, 798 cm$^{-1}$.

NMR (CDCl$_3$, δ): 0.7–2.9 (16H, m), 4.47 (2H, q, J=7.4 Hz), 7.36 (1H, d, J=7.8 Hz), 7.59 (1H, t, J=8.0 Hz), 8.01 (1H, d, J=8.0 Hz), 8.26 (1H, br s), 8.70 (1H, d, J=8.0 Hz), 8.76 (1H, d, J=7.8 Hz), 8.99 (1H, s)

MASS: 395 (M+), 350, 283, 237, 142, 85, 43.

Example 30

The following compound was obtained according to a similar procedure to that of Example 6.

8-(2,3-Dimethylpentanoylamino)-4-oxo-4H-pyrimido[2,1-a]isoquinoline-3-carboxylic acid.

mp: 290°–291° C.

IR (Nujol): 3280, 1720, 1654, 1250, 800 cm$^{-1}$.

NMR (DMSO-d$_6$, δ): 0.8–3.0 (14H, m), 7.83 (1H, d, J=8.4 Hz), 7.86 (1H, t, J=8.4 Hz), 8.15 (1H, d, J=8.4 Hz), 8.92 (1H, d, J=8.4 Hz), 9.01 (1H, d, J=8.4 Hz), 9.06 (1H, s), 10.16 (1H, s).

MASS: 367 (M+), 237, 85, 43.

Example 31

The following compound was obtained according to a similar procedure to that of Example 5.

Ethyl 10-(2-acetoxypropionylamino)-7-methyl-4-oxo-4H-pyrimido[2,1-a]isoquinoline-3-carboxylate.

IR (Nujol): 3315, 1738, 1700, 1680, 1480, 1292, 1238, 1130, 803 cm$^{-1}$.

NMR (CDCl$_3$, δ): 1.45 (3H, t, J=6.8 Hz), 1.64 (3H, d, J=6.8 Hz), 2.28 (3H, s), 2.60 (3H, s), 4.46 (2H, q, J=6.8 Hz), 5.46 (1H, q, J=6.8 Hz), 7.86 (1H, d, J=9.2 Hz), 8.53 (1H, dd, J=9.2 and 2.2 Hz), 8.54 (1H, s), 8.72 (1H, s), 8.94 (1H, d), 8.99 (1H, s).

Example 32

The following compound was obtained according to a similar procedure to that of Example 6.

10-(2-Hydroxypropionylamino)-7-methyl-4-oxo-4H-pyrimido[2,1-a]isoquinoline-3-carboxylic acid from ethyl 10-(2-acetoxypropionylamino)-7-methyl-4-oxo-4H-pyrimido[2,1-a]isoquinoline-3-carboxylate.

mp: >300° C.

IR (Nujol): 3300, 1710, 1692, 1493, 1340, 806 cm$^{-1}$.

NMR (DMSO-d$_6$, δ): 1.39 (3H, d, J=7.4 Hz), 3.50 (1H, m), 4.27 (1H, m), 7.8–8.7 (4H, m), 8.97 (1H, s), 9.56 (1H, br s), 10.25 (1H, br s).

MASS: 341 (M$^+$).

Example 33

The following compound was obtained according to a similar procedure to that of Example 5.

Ethyl 10-(3,3-dimethylbutyrylamino)-7-methyl-4-oxo-4H-pyrimido[2,1-a]isoquinoline-3-carboxylate.

mp: 259°–260.5° C.

IR (Nujol): 3340, 1705, 1692, 1676, 1481, 1142, 797 cm$^{-1}$.

NMR (DMSO-d$_6$, δ): 1.08 (9H, s), 1.36 (3H, t, J=6.8 Hz), 2.31 (2H, s), 3.30 (3H, s), 4.33 (2H, q, J=6.8 Hz), 7.97 (1H, d, J=8.2 Hz), 8.26 (1H, dd, J=8.2 and 2.0 Hz), 8.60 (1H, s), 8.89 (1H, s), 9.31 (1H, d, J=2.0 Hz), 10.36 (1H, s).

Example 34

The following compound was obtained according to a similar procedure to that of Example 6.

10-(3,3-Dimethylbutyrylamino)-7-methyl-4-oxo-4H-pyrimido[2,1-a]isoquinoline-3-carboxylic acid.

mp: >300° C.

IR (Nujol): 3300, 1730, 1686, 1500, 1425, 1143, 860, 807 cm$^{-1}$.

MASS: 367 (M$^+$), 323, 295, 269, 251, 197, 57.

Example 35

The following compound was obtained according to a similar procedure to that of Example 1.

Ethyl 8-bromo-11-nitro-4-oxo-4H-pyrimido[2,1-a]isoquinoline-3-carboxylate.

mp: 256°–256.5° C.

IR (Nujol): 1743, 1638, 1295, 1138, 1080 cm$^{-1}$.

NMR (DMSO-d$_6$, δ): 1.33 (3H, t, J=7.5 Hz), 4.33 (2H, q, J=7.5 Hz), 7.95 (1H, d, J=8.1 Hz), 8.10 (1H, d, J=9.0 Hz), 8.52 (1H, d, J=9.0 Hz), 8.79 (1H, s), 9.04 (1H, d, J=8.1 Hz)

MASS: 393 (M+2), 392, 391 (M$^+$), 348, 319

Example 36

The following compound was obtained according to a similar procedure to that of Example 26.

8-Bromo-11-nitro-4-oxo-4H-pyrimido[2,1-a]isoquinoline-3-carboxylic acid.

mp: 287°–289° C.

IR (Nujol): 1727, 1642, 1085, 813, 785 cm$^{-1}$.

NMR (DMSO-d$_6$, δ): 7.86 (1H, d, J=8.0 Hz), 8.00 (1H, d, J=8.0 Hz), 8.43 (1H, d, J=8.0 Hz), 8.68 (1H, s), 8.93 (1H, d, J=8.0 Hz), 10.50 (1H, br s).

Example 37

The following compound was obtained according to a similar procedure to that of Example 3.

Ethyl 11-amino-8-bromo-4-oxo-4H-pyrimido[2,1-a]isoquinoline-3-carboxylate.

mp: 278°–280° C.

IR (Nujol): 3380, 1720, 1586, 1310, 1280, 830 cm$^{-1}$.

MASS: 363 (M$^+$ +2), 361 (M$^+$).

Example 38

A suspension of ethyl 11-amino-8-bromo-4-oxo-4H-pyrimido[2,1-a]isoquinoline-3-carboxylate (500 mg), in a mixture of acetic acid (25 ml) and 36% hydrochloric acid (5 ml) was heated at 80° C. for 3 hours. The mixture was cooled and diluted with water. The precipitated solid obtained was collected and dissolved into N,N-dimethylformamide (30 ml). The solution was added to an aqueous sodium bicarbonate solution (15 ml). The resulting precipitate was collected, and then dissolved in N,N-dimethylformamide (130 ml). The solution was filtered for removal of insoluble materials. The filtrate obtained was acidified with acetic acid to give 11-amino-8-bromo-4-oxo-4H-pyrimido[2,1-a]isoquinoline-3-carboxylic acid (180 mg).

mp: 283°–284° C.

IR (Nujol): 3400, 1730, 1638, 1200, 800, 780 cm$^{-1}$.

NMR (DMSO-d$_6$, δ): 3.30 (2H, br s), 6.92 (1H, d, J=9.4 Hz), 7.57 (1H, d, J=8.0 Hz), 7.78 (1H, d, J=9.4 Hz), 8.55 (1H, br s), 8.67 (1H, d, J=8.0 Hz), 8.92 (1H, s)

MASS: 335 (M$^+$ +2), 333 (M$^+$).

Example 39

The following compound was obtained according to a similar procedure to that of Example 5.

Ethyl 8-bromo-11-(2,3-dimethylpentanoylamino)-4-oxo-4H-pyrimido[2,1-a]isoquinoline-3-carboxylate NMR (DMSO-d$_6$, δ): 0.5–2.0 (16H, m), 4.34 (2H, q, J=7.0 Hz), 7.74 (1H, d, J=8.0 Hz), 8.15 (1H, d, J=9.4 Hz), 8.83 (1H, d, J=9.4 Hz), 8.89 (1H, s), 8.92 (1H, d, J=8.0 Hz)

MASS: 475 (M$^+$ +2), 474, 473 (M$^+$), 390, 388.

Example 40

The following compound was obtained according to a similar procedure to that of Example 6.

8-Bromo-11-(2,3-dimethylpentanoylamino)-4-oxo-4H-pyrimido[2,1-a]isoquinoline-3-carboxylic acid mp: 238°–239° C.

IR (Nujol): 1740, 1660, 1480, 1197, 805, 780 cm$^{-1}$.

MASS: 447 (M$^+$ +2), 445 (M$^+$).

Example 41

To a stirred mixture containing 10-(2,3-dimethylpentanoylamino)-7-methyl-4-oxo-4H-pyrimido[2,1-a]isoquinoline-3-carboxylic acid (455 mg), triethylamine (0.174 ml) and dry dichloromethane (70 ml) was added slowly ethyl chloroformate (0.12 ml) at 0° C. under an inert atmosphere. After being stirred for 2 hours, a solution of 2-(4-diphenylmethyl-1-piperazinyl)-ethylamine (359 mg) in dry dichloromethane (10 ml) was added dropwise to the reaction mixture at 5° C. After stirring was continued for 12 hours at room temperature, the mixture was concentrated under reduced pressure. The residue was subjected to a column chromatography on silica gel with chloroform-methanol. The eluate was concentrated in vacuo to give residue, which was recrystallized from chloroform-ether to give N-[2-(4-diphenylmethylpiperazin-1-yl)ethyl]-7-methyl-10-(2,3-dimethylpentanoylamino)-4-oxo-4H-pyrimido[2,1-a]isoquinoline-3-carboxamide (0.59 g).

mp: 226°–230° C.

IR (Nujol): 3370, 1660, 1480, 1290, 1148, 1005, 800 cm$^{-1}$.

NMR (CDCl$_3$, δ): 0.5–2.1 (13H, m), 2.1–2.9 (5H, m), 3.1 (2H, m), 4.25 (1H, s), 7.0–7.6 (10H, m), 7.81 (1H, d, J=9.4 Hz), 8.64 (1H, s), 8.77 (1H, dd, J=9.4 and 2.4 Hz), 9.03 (1H, d, J=2.4 Hz), 9.17 (1H, s), 9.50 (1H, m), 9.70 (1H, s).

MASS: 658 (M+), 436, 364, 265, 167.

Example 42

A mixture of 10-(2,3-dimethylpentanoylamino)-7-methyl-4-oxo-4H-pyrimido[2,1-a]isoquinoline-3-carboxylic acid (250 mg) and thionyl chloride (4 ml) was stirred at 10° C. for 30 minutes. The reaction mixture was stirred for 1 hour at room temperature, and then evaporated to dryness in vacuo to give an acid chloride. A mixture of the acid chloride, pyridine (0.1 ml) and dry dichloromethane (60 ml) was cooled to 5° C. A solution of N-(2-hydroxyethyl)nicotinamide (108 mg) in dry dichloromethane was added to the mixture. The reaction mixture was stirred at 5° C. for 1 hour, and allowed to stand at room temperature overnight. The reaction mixture was diluted with chloroform-methanol, and washed with water and brine, dried over magnesium sulfate and evaporated in vacuo. The residue was subjected to a column chromatography on silica gel with chloroform-methanol. The eluate was concentrated in vacuo to give residue, which was recrystallized from chloroform-ether to give 2-(nicotinamido)ethyl 7-methyl-10-(2,3-dimethylpentanoylamino)-4-oxo-4H-pyrimido[2,1-a]isoquinoline-3-carboxylate (0.26 g).

mp: 204°–210° C.

IR (Nujol): 3250, 1730, 1650, 1630, 1226, 1120, 1060, 800 cm$^{-1}$.

NMR (DMSO-d$_6$, δ): 0.5–2.0 (13H, m), 3.27 (3H, s), 3.70 (2H, m), 4.42 (2H, m), 7.3–9.4 (10H, m), 10.32 (1H, s).

EXAMPLE 43

The following compound was obtained according to a similar procedure to that of Example 42.

2-(Nicotinamido)ethyl 10-(2,3-dimethylpentanoylamino)-4-oxo-4H-pyrimido[2,1-a]isoquinoline-3-carboxylate.

mp: 200°–207° C.

IR (Nujol): 3450, 3230, 1735, 1660, 1280, 1142, 1115, 850, 810 cm$^{-1}$.

NMR (CDCl$_3$, δ): 1.6–2.7 (13H, m), 3.90 (2H, m), 4.45 (2H, m), 7.0–9.3 (12H, m)

EXAMPLE 44

The following compound was obtained according to a similar procedure to that of Example 42.

2-(Nicotinamido)ethyl 10-pivaloylamino-7-methyl-4-oxo-4H-pyrimido[2,1-a]isoquinoline-3-carboxylate mp: 205°–210° C.

IR (Nujol): 3400, 3300, 1725, 1650, 1290, 1123, 800 cm$^{-1}$.

NMR (CDCl$_3$, δ): 1.43 (9H, s), 2.45 (3H, s), 3.95 (2H, m), 4.50 (2H, m), 7.1–9.4 (11H, m).

Example 45

To a mixture of N-nicotinoyl-β-alanine (2 g) and triethylamine (1.6 ml) in N,N'-dimethylformamide (200 ml) was added ethyl chloroformate (1.1 ml) at ice bath temperature.

After being stirred for 1 hour at room temperature, ethyl 10-amino-7-methyl-4-oxo-4H-pyrimido[2,1-a]isoquinoline-3-carboxylate (3 g) was added, and then the mixture was heated at 60° C. for 3 hours. The reaction mixture was allowed to stir overnight at room temperature and then concentrated in vacuo. The residue was collected, washed successively with water and methanol and recrystallized from N,N-dimethylformamide to give ethyl 10-[3-(nicotinoylamino)propionylamino]-7-methyl-4-oxo-4H-pyrimido[2,1-a]-isoquinoline-3-carboxlate (3.50 g).

mp 274°–278° C.

IR (Nujol): 3340, 3290, 1700, 1672, 1295, 1144, 860, 800 cm$^{-1}$.

MASS: 473(M+).

Example 46

The following compound was obtained according to a similar procedure to that of Example 6.

10-[3-(nicotinoylamino)propionylamino]-7-methyl-4-oxo-4H-pyrimido[2,1-a]isoquinoline-3-carboxylic acid.

mp>300° C.

IR (Nujol): 3320, 3160, 3050, 1718, 1680, 1490, 1142, 800 cm$^{-1}$.

Example 47

(Preparation of granules or small granules)

| | |
|---|---|
| 10-(2,3-Dimethylpentanoylamino)-7-methyl-4-oxo-4H—pyrimido[2,1-a]isoquinoline-3-carboxylic acid | 500 (g) |
| Sucrose | 9250 |
| Hydroxypropylcellulose | 200 |
| Starch | 50 |

The above ingredients are blended and granulated or grained, in a conventional manner, into granules or small granules.

EXAMPLE 48

(Preparation of capsules)

| | |
|---|---|
| 10-(2,3-Dimethylpentanoylamino)-4-oxo-4H—pyrimido[2,1-a]isoquinoline-3-carboxylic acid | 100 (g) |
| Starch | 1987 |
| Magnesium stearate | 13 |

The above ingredients are blended and filled in hard-gelatin-capsules, in a conventional manner, to give 10,000 capsules, each of which contain 10 mg of an active ingredient.

We claim:

1. Pyrimidoisoquinoline derivatives of the formula:

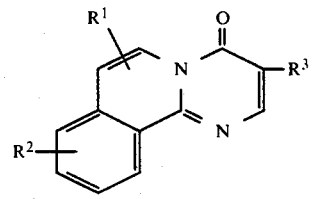

wherein
R$^1$ is hydrogen, halogen or lower alkyl;
R$^2$ is amino, nitro, lower alkanoylamino, hydroxy(lower)alkanoylamino, lower alkanoyloxy(lower)alkanoylamino, pyridinecarbonylamino(lower)alkanoylamino, higher alkanoylamino of up to 20 carbon atoms, lower cycloalkylcarbonylamino, lower alkoxycarbonylamino, lower alkoxalylamino, lower alkanesulfonylamino, or phenylcarbamoylamino, and $R^3$ is carboxy, lower alkoxycarbonyl, pyridinecarbonylamino(lower)alkoxycarbonyl, N-tetrazolylcarbamoyl or N-[2-(4-diphenylmethylpiperazin-1-yl)ethyl]-carbamoyl or pharmaceutically acceptable salts thereof.

2. The compound of claim 1, in which $R^1$ is hydrogen, methyl or bromo, $R^2$ is amino, nitro, pivaloylamino, isobutyrylamino, 2-hydroxypropionylamino, 2-acetoxypropionylamino, 3,3-dimethylbutyrylamino, 2,3-dimethylpentanoylamino, cyclohexylcarbonylamino, ethoxycarbonylamino, ethoxalylamino, mesylamino, 3-(nicotinoylamino)propionylamino or phenylureido, and $R^3$ is carboxy, ethoxycarbonyl, 2-nicotinamidoethoxycarbonyl, N-(1H-tetrazol-5-yl)carbamoyl or N-[2-(4-diphenylmethylpiperazin-1-yl)ethyl]carbamoyl.

3. A compound according to claim 1, in which $R^1$ is 7-lower alkyl or hydrogen.

4. The compound of claim 3, which is 10-(2,3-dimethylpentanoylamino)-7-methyl-4-oxo-4H-pyrimido[2,1-a]isoquinoline-3-carboxylic acid or pharmaceutically acceptable salts thereof.

5. The compound of claim 3, which is 10-(2,3-dimethylpentanoylamino)-4-oxo-4H-pyrimido-[2,1-a]isoquinoline-3-carboxylic acid or pharmaceutically acceptable salt thereof.

6. The compound of claim 3, which is 10-pivaloylamino-7-methyl-4-oxo-4H-pyrimido[2,1-a]-isoquinoline-3-carboxylic acid or pharmaceutically acceptable salts thereof.

7. The compound of claim 3, which is ethyl 10-isobutyrylamino-7-methyl-4-oxo-4H-pyrimido-[2,1-a]isoquinoline-3-carboxylate or pharmaceutically acceptable salts thereof.

8. The compound of claim 3, which is 2-(nicotinamido)ethyl 7-methyl-10-(2,3-dimethyl-pentanoylamino)-4-oxo-4H-pyrimido[2,1-a]isoquinoline-3-carboxylate or pharmaceutically acceptable salts thereof.

9. A pharmaceutical composition comprising, as an active ingredient, (a) an antiallergically effective amount of a pyrimidoisoquinoline of claim 1 or pharmaceutically acceptable salt thereof, and (b) a pharmaceutically acceptable carrier.

10. A method of treating allergies in a patient subjected to the allergies comprising administering to the patient an antiallergic amount of a pyrimidoisoquinoline of claim 1 or pharmaceutically acceptable salt thereof to effect such treatment.

* * * * *